United States Patent [19]

Ishikawa et al.

[11] Patent Number: 4,579,631

[45] Date of Patent: Apr. 1, 1986

[54] MEASUREMENT OF OXYGEN CONCENTRATION

[75] Inventors: Yoichi Ishikawa, Houya; Yoshio Iwami, Tokyo, both of Japan

[73] Assignee: Ishikawa Seisaku-sho Co., Ltd., Tokyo, Japan

[21] Appl. No.: 536,436

[22] Filed: Sep. 27, 1983

[30] Foreign Application Priority Data

Oct. 9, 1982 [JP] Japan .................................. 57-153644

[51] Int. Cl.[4] ............................................ G01N 27/46
[52] U.S. Cl. .................................... 204/1 T; 204/403; 204/415; 435/291; 435/807
[58] Field of Search ............... 204/1 P, 1 T, 415, 400, 204/403; 435/291, 807

[56] References Cited

U.S. PATENT DOCUMENTS

| | | | |
|---|---|---|---|
| 3,503,861 | 3/1970 | Volpe | 204/415 |
| 3,701,716 | 10/1972 | Deuringer et al. | 435/291 |
| 3,793,154 | 2/1974 | Efthymiou | 435/291 |
| 3,838,034 | 9/1974 | Groves | 435/291 |
| 3,988,233 | 10/1976 | Gamer | 204/415 |
| 4,024,042 | 5/1977 | Enfors et al. | 204/415 |
| 4,172,770 | 10/1979 | Semersky et al. | 435/291 |
| 4,230,537 | 10/1980 | Delente | 204/415 |
| 4,248,712 | 2/1981 | Baumeister | 204/415 |
| 4,267,276 | 5/1981 | Crawford et al. | 204/1 T |

Primary Examiner—T. Tung
Attorney, Agent, or Firm—Birch, Stewart, Kolasch & Birch

[57] ABSTRACT

A system is disclosed for measuring the oxygen concentration in a fluid contained in a fermentation vessel, comprising a fermentation vessel containing a nozzle aperture disposed in the wall thereof, an electrode holder slidably disposed within the nozzle aperture, the electrode holder being provided at one end thereof with an oxygen permeable membrane which provides a wall across the aperture in the vessel for contact with the fluid to be examined, a diaphragm oxygen electrode mounted in the electrode holder of the fermentation vessel so that the diaphragm of the electrode and the oxygen permeable membrane are in close contact with each other, whereby the oxygen concentration of the fluid contained in the fermentation vessel is measured. A method for measuring the oxygen concentration in a fluid contained in a fermentation vessel is also disclosed.

18 Claims, 5 Drawing Figures

MEASUREMENT OF OXYGEN CONCENTRATION

BACKGROUND OF THE INVENTION

The present invention relates to the construction of a diaphragm type oxygen electrode and a method of measuring oxygen concentration using such an electrode. The use of an oxygen-permeable membrane between an oxygen electrode and a substance being examined makes it easy to replace the oxygen electrode and also enables the safe and simple steam sterilization of the tank containing the substance being examined.

When measuring the oxygen concentration of a gaseous or liquid phase in a tank, it is common practice to mount a diaphragm type oxygen electrode directly into the tank. This, however, makes it difficult to replace the electrode if it fails because when the electrode is removed, the liquid or gas in the tank might leak from the area where the electrode was mounted. Especially in the case of a fermentation tank, if the electrode is removed when measuring the oxygen concentration of the liquid or gaseous phase in the tank, various contaminants might get into the tank resulting in the contamination of the reaction. In practice it is impossible to replace the electrode in such a tank.

Therefore a system is required which makes it possible to replace the electrode in a tank containing a substance to be examined without influencing the substance being examined.

Since steam sterilization of the oxygen electrode in a fermentation tank must be conducted with the electrode in position in the tank, the electrode must be of high quality to withstand the harsh condition. It must have a high heat resistance, pressure resistance and moisture resistance. Further, in the measurement of liquid-phase oxygen in a shake flask, the electrode used therefor must meet the additional requirements of being small in size and lightweight because the electrode is also shaken during the measurement. Such an electrode must also meet the design requirement that it should not project inward from the wall surface of the flask so that it is not affected by stirring. No oxygen electrode or measuring method that satisfies all these requirements is presently available.

SUMMARY OF THE INVENTION

In order to solve these problems, the present invention provides a novel diaphragm type oxygen electrode and a method of measuring oxygen concentration using such an electrode.

According to the present invention, part of a tank wall in contact with a liquid or gas being examined within the tank is constituted of an oxygen-permeable membrane, and a diaphragm type oxygen electrode is mounted outside the tank with the diaphragm thereof attached tightly to the oxygen-permeable membrane so as to measure the oxygen concentration of the liquid or gas.

According to the method of the present invention, it is possible to further enhance the measurement accuracy of the oxygen in the liquid or gas by providing a liquid between the oxygen-permeable membrane and the diaphragm. Any suitable intervening liquid may be used such as silicone oil, and other types of oil, ethylene glycol, vaseline and the like. This liquid remains around the point of contact between the diaphragm and the oxygen-permeable membrane when they are attached tightly to each other, thus forming a barrier which prevents oxygen entering this area from escaping around the outer periphery of the electrode. This liquid is therefore useful for filling the gap between the two membranes (diaphragm and membrane). In practice, this effect can be attained by applying a small amount of the liquid to the end of the electrode and mounting the electrode properly so that the liquid-applied part is attached tightly against the oxygen-permeable membrane.

The present invention also provides an improved diaphragm type oxygen electrode featuring the incorporation of a liquid retaining membrane over the outside of the oxygen-permeable membrane. The liquid-retaining membrane comes into contact with the liquid being examined. The diaphragm type oxygen electrode with this structure enables the correct and stable measurement of liquid-phase oxygen alone, without being affected by gaseous oxygen. The device of this invention is best suited to the measurement of liquid-phase oxygen in a tank, such as a fermentation tank or an aeration tank, where the measurement is conducted while air is passed into the tank.

As described above, the diaphragm type oxygen electrode according to this invention is provided structurally separate from the tank in which the oxygen-permeable membrane is provided. Therefore, the diaphragm type oxygen electrode can be mounted after performing steam sterilization on the tank. It is also possible to hold the oxygen-permeable membrane securely from the outside thereof by a support means so that the membrane can withstand the internal pressure produced during the steam sterilization. If the electrode is mounted after the completion of the steam sterilization, the exposure of the electrode to the harsh sterilization conditions can be avoided.

Thus, the present invention embraces a diaphragm type oxygen electrode used in the above-described method and is characterized by a diaphragm which is attached tightly against an oxygen-permeable membrane incorporated into the wall of a tank containing the substance being examined.

BRIEF DESCRIPTION OF THE DRAWINGS:

The following drawings illustrate various embodiments of the present invention, wherein.

Figure 1:
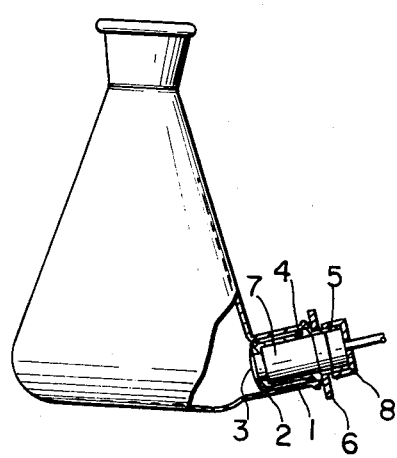
FIG. 1 is a drawing illustrating the adaptation of the electrode of the invention to the measurement of liquid-phase oxygen in a shake flask.

DETAILED DISCUSSION:

Referring now to FIG. 1 there is seen a oxygen-permeable membrane 3 fixed to an electrode holder 10 via an O-ring 2, the electrode holder 10 being slidably secured to a nozzle 1 of the flask by a second O-ring 4. The nozzle and electrode holder are secured hermetically in position by the two O-rings 2 and 4. It is preferred to provide a flange 6 in threaded engagement with an external thread 5 on the electrode holder, such a flange serving as a guide for the proper positioning of the electrode holder, and it can also be used as a handle for facilitating the mounting and demounting of the holder.

After steam sterilization of the flask, a diaphragm type of oxygen electrode 7 is fitted into the holder and then a cap nut 8 is tightened onto the external thread of the holder so that the diaphragm 9 (FIG. 3) of the electrode is fixed tightly to the oxygen-permeable membrane 3. This arrangement is advantageous in that it eliminates the necessity of heat sterilization of the electrode, minimizes the risk of damage to the electrode without influencing the measuring system adversely in the event of failure of the electrode. In the case of fermentation tank having a capacity of over 30 liters, if the oxygen-permeable membrane is mounted in the manner described above, it may suffer damage due to too-large of a load applied during steam sterilization. In this case, it is recommended that, before setting the electrode, a compression rod be inserted so that its end touches the oxygen-permeable membrane and after sterilization, the compression rod is removed and the diaphragm type oxygen electrode is mounted. In so doing, it is possible to eliminate the possibility of excessive pressure loading on the membrane during the steam sterilization operation. The compression rod preferably has the same diameter and shape as the oxygen diaphragm electrode that is to be mounted.

Figure 2:
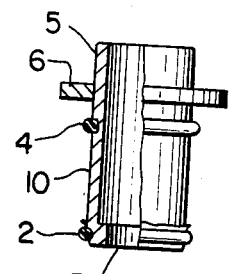
FIG. 2 illustrates the fitting of an oxygen-permeable membrane to an electrode holder.

FIG. 2 illustrates the fitting of the oxygen permeable membrane 3 to the holder 10 by the O-ring 2.

Figure 3:
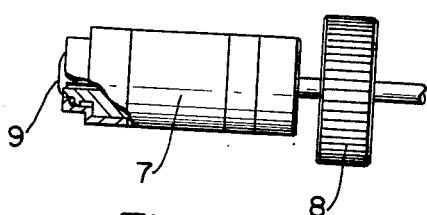
FIG. 3 is a detailed illustration of the electrode of the present invention.
Figure 4:
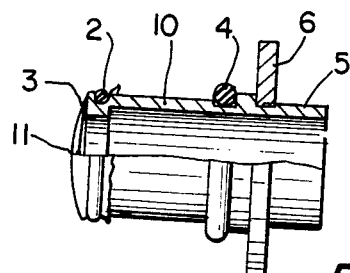
FIG. 4 shows an embodiment relating to a liquid-retaining membrane 11 according to the present invention.

In FIG. 4, a liquid-retaining membrane 11, such as gauze, is positioned so that it is superimposed onto the outside of the oxygen permeable membrane 3 at the part where the holder is in contact with the fluid, and is fixed to the outer periphery of the holder by the O-ring 2 as shown in FIG. 4. The holder is then slidably secured to the flask nozzle 1 by the remaining O-ring 4 provided behind the O-ring 2. After sterilizing the flask in an autoclave, the oxygen electrode 7 shown in FIG. 3 is placed in the holder and then the cap nut 8 is screwed onto the threaded portion 5 of the holder to secure it. When about 50 ml of a 2% aqueous solution of sodium sulfite, which contains no oxygen gas, is introduced into a 500 ml flask, the surface of the introduced liquid reaches the lower end of the oxygen-permeable membrane attached to the electrode. The flask accordingly contains therein the gas phase of air and the liquid phase. When the flask is shaken, the output of the electrode shows zero. It is understood from this simple test that the gas phase does not have influence on the electrode. This is due to the fact that even if the test liquid runs out, the liquid retainer is already wet and retains liquid therein, enabling the measurement of only the oxygen remaining dissolved in the liquid.

The present invention also concerns a flask of a construction which makes it suitable for use as a shake flask for aerobic culture, especially in the field of fermentation chemistry. This flask is particularly advantageous in that it enables a continuous controlled supply of liquid-phase oxygen to the culture medium.

In conventional shake flasks used for aerobic culture, the supply of oxygen and the discharge of the gases produced by fermentation in the flask have been realized by means of natural convection through an aeration plug such as a cotton wool plug or a foamed silicone plug adapted to the flask. With such an aeration plug, however, since the movement of oxygen or other gases into or out of the system is effected by natural diffusion, the rate of movement cannot be increased beyond a fixed level, so that when the cell concentration in the system increases, the supply of oxygen into the culture medium becomes insufficient because of the limited rate of diffusion. It has been observed that when the liquid-phase oxygen in the medium has almost run out, the gaseous-phase oxygen in the flask is also reduced to 1/5 to 1/10 or less of the oxygen concentration in the atmosphere. That is, it has been confirmed that the oxygen supply to the medium is determined by the limited oxygen diffusion through the aeration plug. This not only restricts the cell growth rate but also increases the concentration of $CO_2$, which is a metabolic product, in the system, resulting in harmful effects to the system and a reduction of the pH of the medium. Generally, it is very difficult to determine the interrelation between a culture in a flask and a culture in a mini-jar to which oxygen is supplied. This is considered to be mostly due to the limited oxygen supply rate in the flask.

The present invention has solved this problem by providing a flask having a construction in which oxygen is forcibly fed or sucked into the flask having an aeration plug and the discharge or introduction of the gases produced is effected through the same plug. Thus, oxygen is forcibly supplied to the gaseous-phase section in the flask to supply oxygen into the medium. The aeration plug which is used as an oxygen supply port in a conventional device is utilized as a discharge port and an inlet port in this invention.

Figure 5:
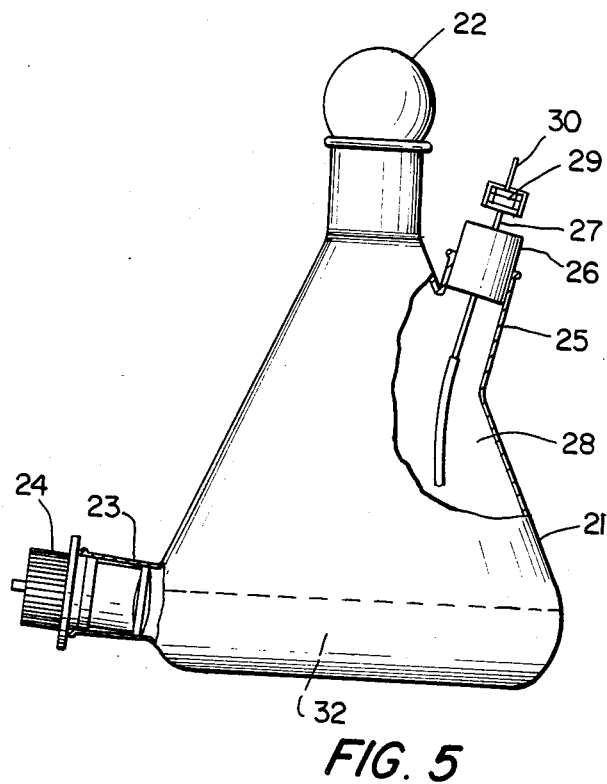
FIG. 5 is a schematic illustration of another embodiment of the present invention including an aeration plug and an air transfer nozzle.

FIG. 5 is a schematic illustration of the shake flask 21 used for the fermentation of a culture in the system. An opening 23 is provided in the lower side wall where a culture medium 32 is introduced, and an oxygen electrode 24 is fitted therein to allow for the measurement of liquid-phase oxygen in the medium. A cotton wool plug 22, which serves as an aeration plug, is set in the top of the flask. Another opening 25 is provided in the upper side wall of the flask where the gaseous phase of the system will collect, and an air transfer nozzle 27 is mounted therein.

The secured part of the nozzle 27 passes through a rubber plug 26 and a stainless steel pipe portion 27a of the nozzle 27 communicates an air layer 28 in the flask with the outside. A filter 29 and an air inlet (and outlet) 30 are provided at the outer end of the pipe. As air is forcibly supplied or sucked into the system through the air inlet, the metabolic product gases such as carbon dioxide are discharge from the system. The rate of air forcibly supplied through the nozzle should preferably be below 1VVM, although the air rate can vary depending on the tightness of the cotton wool plug in the flask. If the air rate is higher than that, a positive pressure may develop in the flask, causing the cotton wool plug to rise up and create a space between the plug and the flask wall, raising the risk of the entrance of contaminants into the system.

When air is sucked into the system through the nozzle, the cotton wool plug should be attached even more firmly to the flask wall. If a flow rate of air is too high during either suction or pressure feeding of the air, the liquid to be examined is easy to evaporate. Accordingly it is preferable to conduct the suction or pressure feeding of air intermittently. A preferable flow rate of air is below 1VVM, which corresponds to a volume of the flask used per minute. effected by using a peristaltic pump with a rubber tube attached to the air outlet 30. In this case, the filter 29 can be eliminated. Although the adaptation of this invention to a conical flask has been exemplified in this embodiment, the invention can be similarly applied to a Sakaguchi flask.

The application of this invention can ensure an adequate supply of oxygen to the gaseous-phase section of the flask, providing a substantial increase in the amount of liquid-phase oxygen in the flask, so that it is possible to increase the amount of culture medium and raise the cell concentration therein. The interrelation between the flask culture and the mini-jar culture can be also determined. As an aeration plug, it is possible to use, besides a cotton wool plug, other generally employed types of plugs such as foamed silicone plugs, foamed urethane plugs and the like.

The invention being thus described, it will be obvious that the same may varied in many ways. Such variations are not to be regarded as a departure from the spirit and scope of the present invention, and all such modifications as would be obvious to one skilled in the art are intended to be included within the scope of the following claims.

What is claimed:

1. A method of measuring the oxygen concentration in a fluid contained in a fermentation vessel, comprising
   providing the fermentation vessel with a nozzle aperture disposed in its wall,
   slidably positioning an electrode holder within the nozzle aperture, said electrode holder being provided at one end with an oxygen permeable membrane which provides a wall across said aperture in said vessel for contact with the fluid to be examined,
   subjecting the vessel to steam sterilization,
   mounting a diaphragm oxygen electrode in the electrode holder of the fermentation vessel so that the diaphragm of the electrode and the oxygen permeable membrane are in close contact with each other and,
   measuring the oxygen concentration of the fluid contained in the fermentation vessel.

2. The method of claim 1 wherein an intervening liquid is provided between said oxygen-permeable membrane and said diaphragm.

3. The method of claim 2 wherein before mounting the electrode in the electrode holder, the surface of the oxygen permeable membrane is provided with the intervening liquid which is disposed between said membrane and the diaphragm of the electrode after the electrode has been mounted into the holder, said liquid remaining around the point of contact between the diaphragm and the oxygen permeable membrane to thereby form a barrier which prevents oxygen from escaping around the periphery of the electrode.

4. The method as recited in claim 3, wherein the intervening liquid is selected from the group consisting of silicone oil, ethylene glycol and vaseline.

5. The method as recited in claim 2, wherein before mounting the electrode in the electrode holder, the end of the electrode is provided with the intervening liquid which is disposed between said membrane and the diaphragm of the electrode after the electrode has been mounted into the holder, said liquid remaining around the point of contact between the diaphragm and the oxygen permeable membrane to thereby form a barrier which prevents oxygen from escaping around the periphery of the electrode.

6. The method as recited in claim 5, wherein the intervening liquid is selected from the group consisting of silicone oil, ethylene glycol and vaseline.

7. The method of claim 1, wherein said oxygen-permeable membrane is independently supported from the outside by a support means during the steam sterilization so that said membrane can withstand the internal pressure created when said steam sterilization is conducted.

8. The method as recited in claim 1, wherein the fluid is a liquid.

9. The method as recited in claim 8, wherein the electrode holder is further provided with a liquid-retaining membrane positioned outside of said oxygen permeable membrane to contact the liquid to be examined whereby a thin layer of liquid is formed and retained in said liquid-retaining membrane.

10. The method as recited in claim 9, wherein the liquid-retaining membrane is composed of gauze material.

11. A system for measuring the oxygen concentration in a fluid contained in a fermentation vessel, comprising
    a fermentation vessel containing a nozzle aperture disposed in the wall thereof,
    an electrode holder slidably disposed within the nozzle aperture, said electrode holder being provided at one end thereof with an oxygen permeable membrane which provides a wall across said aperture in said vessel for contact with the fluid to be examined,
    a diaphragm oxygen electrode mounted in the electrode holder of the fermentation vessel so that the diaphragm of the electrode and the oxygen permeable membrane are in close contact with each other whereby the oxygen concentration of the fluid contained in the fermentation vessel is measured.

12. The system as recited in claim 11, wherein the fluid is a liquid.

13. The system as recited in claim 12, which further comprises a liquid-retaining membrane positioned outside of said oxygen permeable membrane to contact the liquid to be examined whereby a thin layer of liquid is formed and retained in said liquid-retaining membrane.

14. The system as recited in claim 13, wherein the liquid-retaining membrane is composed of gauze material.

15. The system as recited in claim 11, which further comprises an intervening liquid located between said oxygen permeable membrane and said diaphragm.

16. The system as recited in claim 15, wherein the intervening liquid is selected from the group consisting of silicone oil, ethylene glycol and vaseline.

17. The system as recited in claim 11, wherein the vessel is a shake flask.

18. The system as recited in claim 17, wherein the shake flask is provided with an aeration plug and is further provided in a wall surface thereof with a nozzle through which air can be forcibly supplied or sucked in.

* * * * *